(12) United States Patent
McAllen, III et al.

(10) Patent No.: US 6,273,893 B1
(45) Date of Patent: Aug. 14, 2001

(54) ABSORBABLE RIVET/PIN APPLIER FOR USE IN SURGICAL PROCEDURES

(75) Inventors: John McAllen, III, Point Pleasant; David W. Overaker, Annandale; Kevin L. Cooper, Warren, all of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/437,457

(22) Filed: Nov. 10, 1999

(51) Int. Cl.⁷ .................................................. A61B 17/56
(52) U.S. Cl. .............................................................. 606/104
(58) Field of Search ............................ 606/104; 227/132, 227/147; 81/463; 29/525.06

(56) References Cited

U.S. PATENT DOCUMENTS

| 4,493,205 | * | 1/1985 | Ramey ...................................... 72/391 |
| 4,590,928 | | 5/1986 | Hunt et al. . |
| 5,268,001 | | 12/1993 | Nicholson et al. . |
| 5,398,861 | * | 3/1995 | Green ...................................... 227/132 |
| 5,662,658 | * | 9/1997 | Wenstrom, Jr. ....................... 606/104 |
| 5,741,268 | * | 4/1998 | Schutz ................................... 606/104 |
| 5,881,942 | * | 3/1999 | Bergamini ............................. 227/132 |
| 5,904,284 | * | 5/1999 | Lin ......................................... 227/132 |

FOREIGN PATENT DOCUMENTS

2452892 * 12/1980 (FR) ..................................... 227/132

* cited by examiner

Primary Examiner—Jeffrey A. Smith
Assistant Examiner—Eduardo C. Robert (57) ABSTRACT

This invention describes a rivet applier delivering orthopedic fasteners into a patient. The rivet applier inserts the rivet body then drives a pin into the rivet body to fix the rivet in position. The rivet applier contains a hammer, hammer spring, firing pin and receiver to deploy rivets. The hammer of the rivet applier is attached to loading grips. The loading grips cock the hammer. A rivet is inserted into the receiver. Upon releasing the hammer, the hammer drives the firing pin and the firing pin inserts the rivet pin into the rivet.

13 Claims, 8 Drawing Sheets

# ABSORBABLE RIVET/PIN APPLIER FOR USE IN SURGICAL PROCEDURES

FIELD OF THE INVENTION

The field of art to which this invention relates is surgical instruments, in particular an applier for delivering an absorbable orthopaedic fastener. More specifically this invention relates to a single-shot rivet applier that drives an absorbable polymer rivet and pin for fixating of medical devices to bone, especially hard tissue of the cranium or face, for plastic or reconstructive surgical procedures.

BACKGROUND OF THE INVENTION

There are currently a variety of metallic fasteners and appliers or drivers to deliver the fastener for attaching bone plates to fracture and surgery repair sites; spinal, cranial, and maxillo-facial plates have all been fastened using metal screws. The disadvantage of metal screws and other fasteners is that they are permanent and may need to be removed through a second surgical procedure. If they remain in the body, tissue atrophy and subsequent loosening of the device may occur. In addition, metallic and especially plastic screws, including absorbable polymer screws, quite often require tapping threads into the bone; a laborious task that slows the surgical procedure and can lead to poor fixation from stripping of the threaded bone.

Metallic wire or suture can be used to attach plates to bone. This technique requires a tedious method of drilling numerous holes, guiding the wire through the holes, tying and bending the wire and then cutting excess wire away to prevent irritation of soft tissues.

Furthermore, several rivet patents relate to devices which are inserted into a hole and then deployed by driving a member upwards, or proximally, through or into a radially flexible portion of the device. This requires that the hole be deeper than the depth of the deployed device in order to leave enough room to fully insert the device with some type of driver before deployment. Such designs are undesirable for surgical applications where only a thin layer of bone is available for attachment or it is not possible to drill beyond the depth of the thin bone layer for fear of damaging underlying soft tissues, such as in cranial and maxillo-facial surgical procedures. In such cases, the required length of the fastener for adequate fastening strength is very close to the total thickness of the bone.

U.S. Pat. No. 4,590,928 describes an anchor consisting of an elongated cylindrical body with a tapered coaxial channel and radially flexible legs and a pin insertable into the end having the head, the proximal end. The body is placed into a hole formed in bone and the pin is inserted into the channel to expand the legs radially into the surrounding bone. The body and pin are of biocompatible material and the body contains carbon fibers embedded in and extending longitudinally along its interior. Since carbon fibers are not absorbed by or resorbed within the body, this fastener is only partially absorbable.

This U.S. Pat. No. 4,590,928, describes a fastener having a solid pin. It is well known that the material properties, such as Young's modulus of elasticity and is the material yield stress, of bone tissue change significantly with age and vary significantly among individuals of the same age and sex. Having a solid pin therefore limits the fastening ability of the device since the pin cannot deform if the surrounding bone is so stiff that the legs cannot expand radially outwards.

In such a case where the surrounding bone is stiffer than that for which the device was designed and the pin is solid, the large force required to drive the rigid pin into the tapered hole will be such that either the legs will be deformed and rendered useless or the pin will be crushed. A radially compressible or flexible pin that could deform radially inwards to fit the internal passage under high insertion load conditions would give the fastener better performance over a wider range of bone material properties.

U.S. Pat. No. 5,268,001 describes an apparatus for emplacement of a single bone fastener in a bone. The apparatus consists of a holder for holding an expandable sleeve in position within a pre-drilled hole in bone. A plunger moveable in relation to the holder forces a pin into the bore of the expandable sleeve. An attached means for separating the expandable sleeve from the holder (i.e. annular cutter) then cuts the expandable sleeve, thereby releasing the sleeve from the holder. Typical procedures require more than one fastener and varying amounts of application force.

Therefore, what is needed in the art is a novel absorbable fastener for cranial, maxillo-facial, and other reconstructive surgical applications in which the fastener is inserted into a hole having the same depth as the fastener and is deployed by driving a radially compressible member downwards, or distally, into a flexible body of the fastener from above. The current invention discloses an applier for such a device wherein the applier can fire a rivet fastener with minimum force thereby speeding and simplifying the procedure. The impact applier consists of a firing mechanism that can produce varying degrees of force required for different surgical applications.

SUMMARY OF THE INVENTION

We have discovered a rivet applier comprising of a handle with a central axis, hammer chamber, a hammer, biasing spring, a grip loader, a firing pin, and a receiver. The handle has a hammer chamber adjacent to the proximal end of the body and substantially parallel to the central axis. The hammer is slidably mounted within the hammer chamber of the handle. At the distal end of the applier is a receiver for retaining rivets. The receiver is in mechanical communications with a firing pin slidably mounted with the hammer in the applier in a central passage. The central passage provides mechanical communications between the hammer and the firing pin. Three stops, a hammer stop, a firing pin stop, and a firing pin guide stop are provided in the device which insure precise travel of the rivet pin upon firing. The grip loader is mechanically linked to the hammer and provides a means for moving the hammer. The proximal chamber opening is releasably capped to provide access to the spring.

Optionally a trigger mechanism may be provided. The trigger mechanism is composed of a trigger pin having a notch and a trigger spring for biasing the trigger notch. The trigger pin will generally be placed substantially perpendicular to the horizontal axis and is slidably mounted in this perpendicular direction The hammer is mechanically linked to a trigger mechanism for restraining the hammer in a first position and being capable of releasing the hammer in cooperation with the movement of the trigger to allow the hammer to move to a second position.

The rivet is manually loaded via a press-fit to the receiver at the distal end of the rivet applier. Firing the trigger advances the rivet out of the rivet applier and pushes the rivet pin into the rivet thereby securing the rivet in the patient.

BRIEF DESCRIPTION OF THE FIGURES

FIGS. 7A and 7B are a cross-sectional view of the barrel of the rivet.

FIGS. 8A and 8B are cross-sectional view of second embodiment of the rivet applier.

DETAILED DESCRIPTION OF THE INVENTION

Figure 1:
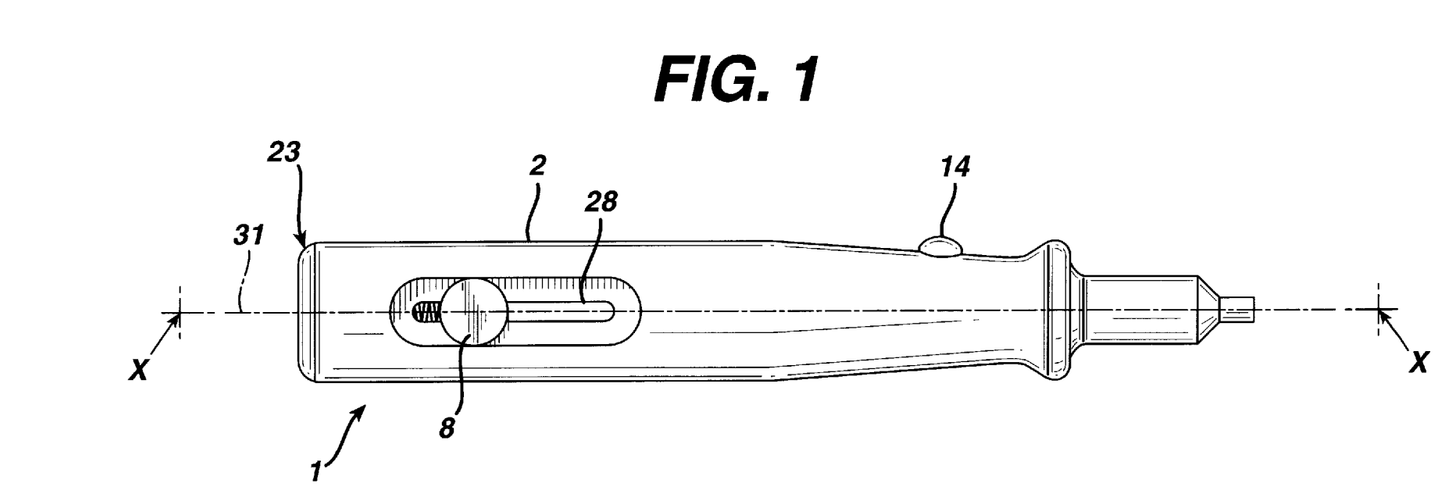
FIG. 1 is a perspective view of the rivet applier.
Figure 2:
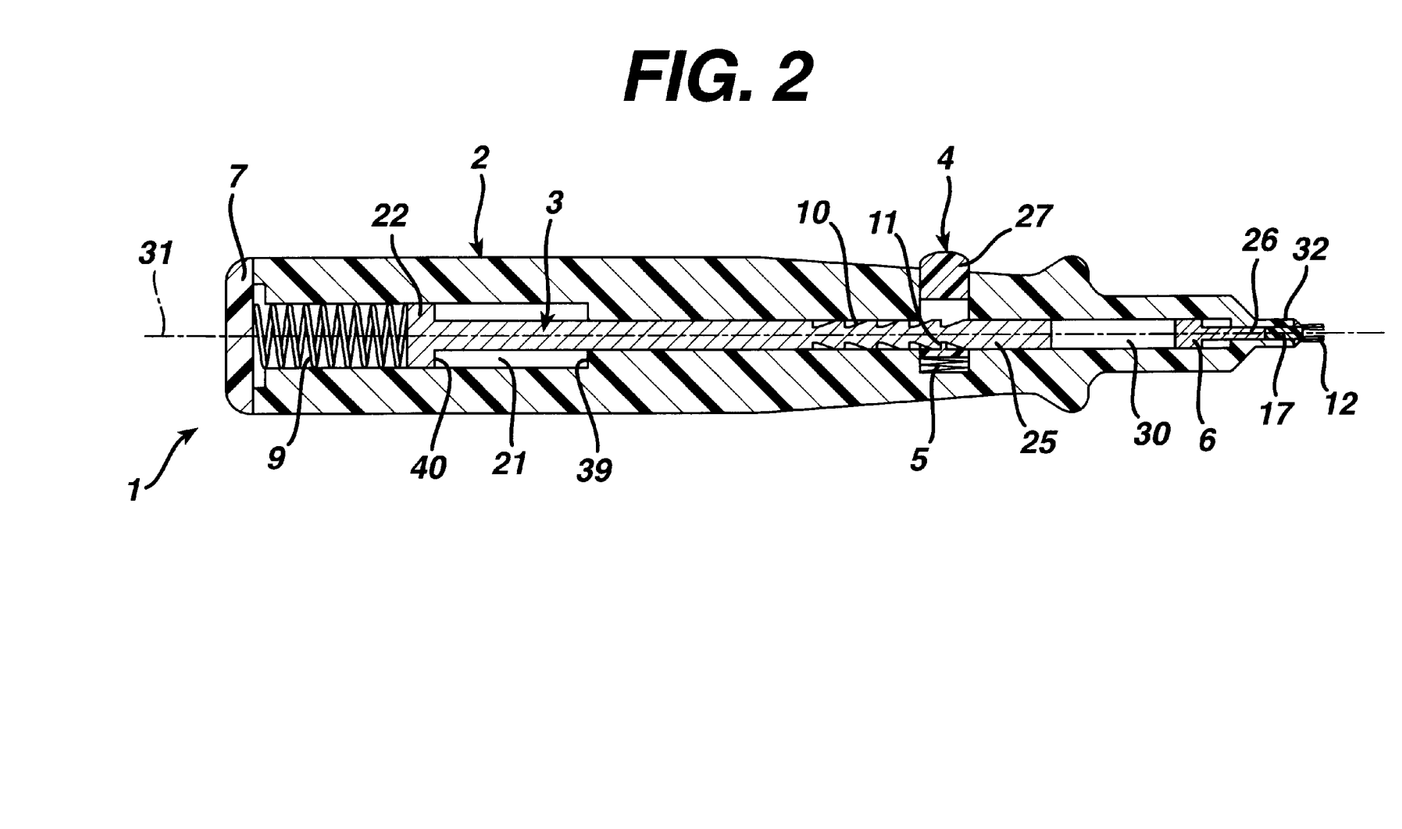
FIG. 2 is a cross-sectional view of one embodiment of a rivet applier taken along the line X—X.

The present invention discloses a single-shot rivet applier 1 comprised of a body 2 with a central axis 31, which is illustrated in FIGS. 1 and 2. Inside the body 2, adjacent to the proximal end 23 and substantially aligned with the central axis 31, is a hammer chamber 21, hammer 3, hammer spring 9. In one embodiment of the invention a removable cap 7 seals the hammer chamber 21 at the proximal end of the applier 1. The hammer is composed of a hammer head 22 and extending therefrom is hammer striker rod 25. The hammer is biased by hammer spring 9 toward the distal end of the applier. Loading grips 8 are mechanically linked to the hammer 3 via openings 28 and may extend substantially perpendicular or parallel to the central axis 31 (see FIGS. 7 and 8).

A central passage 30, extends from the hammer chamber 21 to the receiver 32. The hammer striker rod 25 is slidably mounted within the central passage 30. A firing pin 6 is also slidably mounted within the central passage 30 in mechanical communications with the receiver 32 via striker pin 26.

A trigger mechanism 4, may optionally be present composed of a trigger pin 27 with a trigger notch 11 and a trigger spring 5 to bias the trigger notch 11 against the hammer notches 10. The trigger mechanism 4 is generally placed substantially perpendicular to the horizontal axis 31.

When loading the applier 1 the loading grips 8 are pulled toward the proximal end 23 of the applier 1 compressing the hammer spring 9. The hammer notches 10, (see FIG. 2) engage the trigger notch 11, which is part of the trigger mechanism 4.

Figure 6:
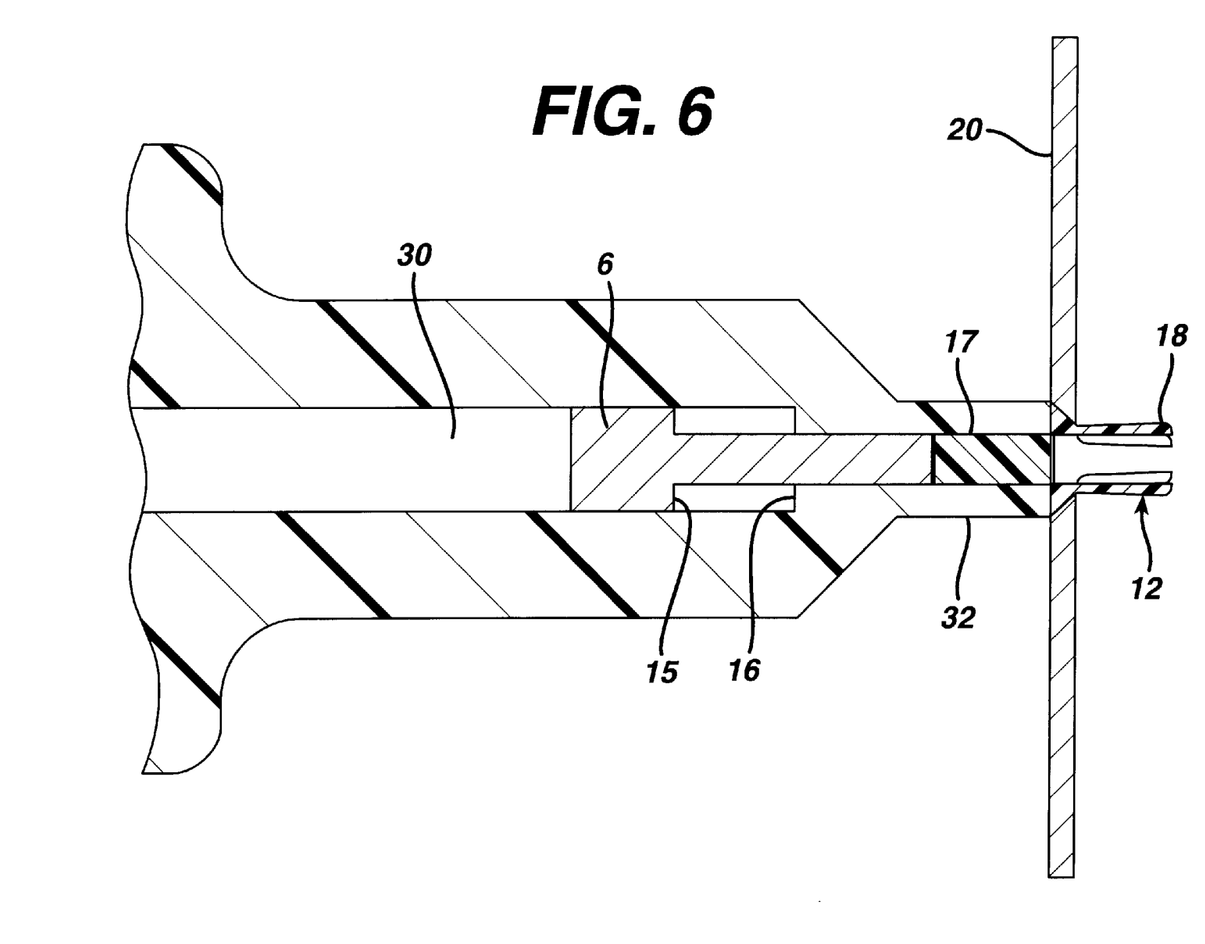
FIG. 6 is a cross-sectional view of the barrel of the rivet applier before deploying a rivet into a plate.

The rivet 12, (see FIG. 6), is comprised of a rivet pin 17, and a rivet body 18. The rivet 12 is loaded either by inserting the rivet pin 17 into the receiver 32 or by placing the receiver 32 over the rivet pin 17.

Figure 3:
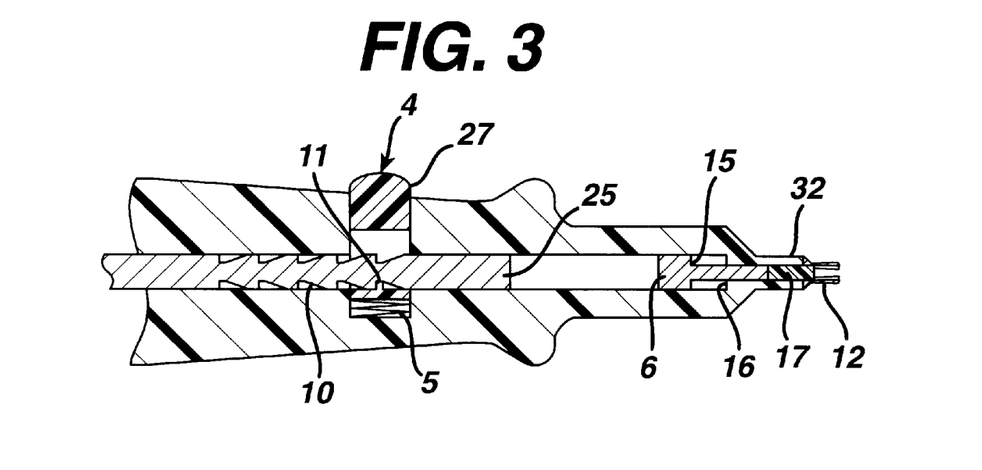
FIG. 3 is a close up cut away view of the cocked rivet applier along line X—X.
Figure 4:
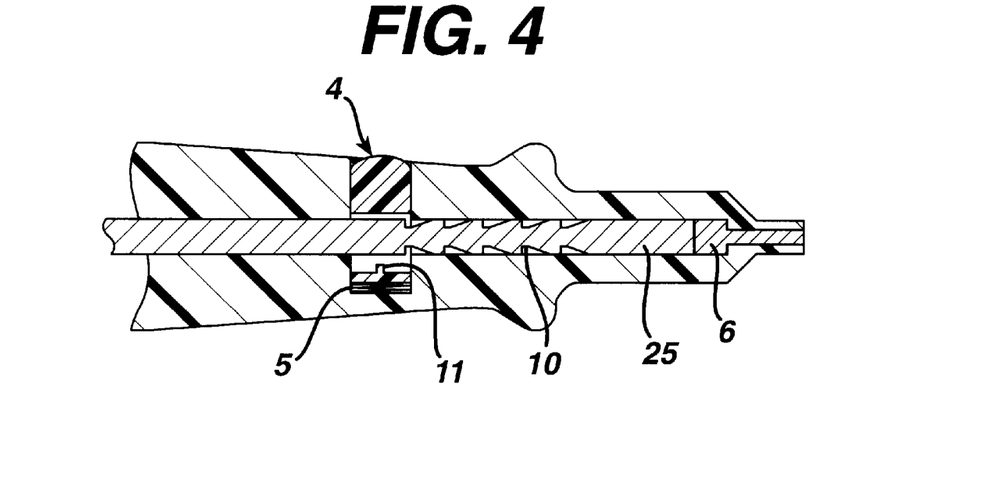
FIG. 4 is a close up cut away view of the fired rivet applier along line X—X.
Figure 5:
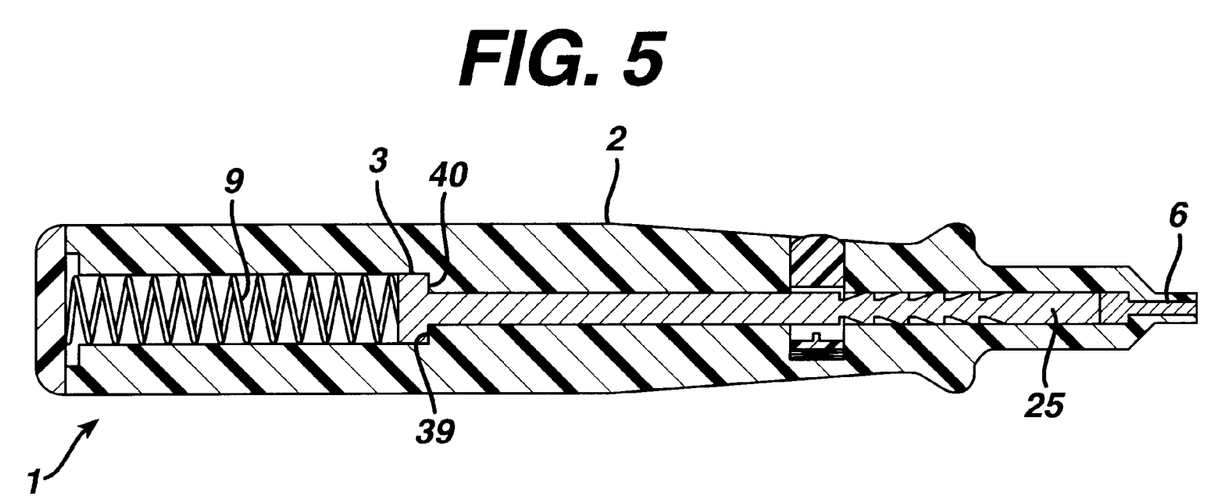
FIG. 5 is a perspective view of the fired rivet applier.
Figures 7A, 7B:
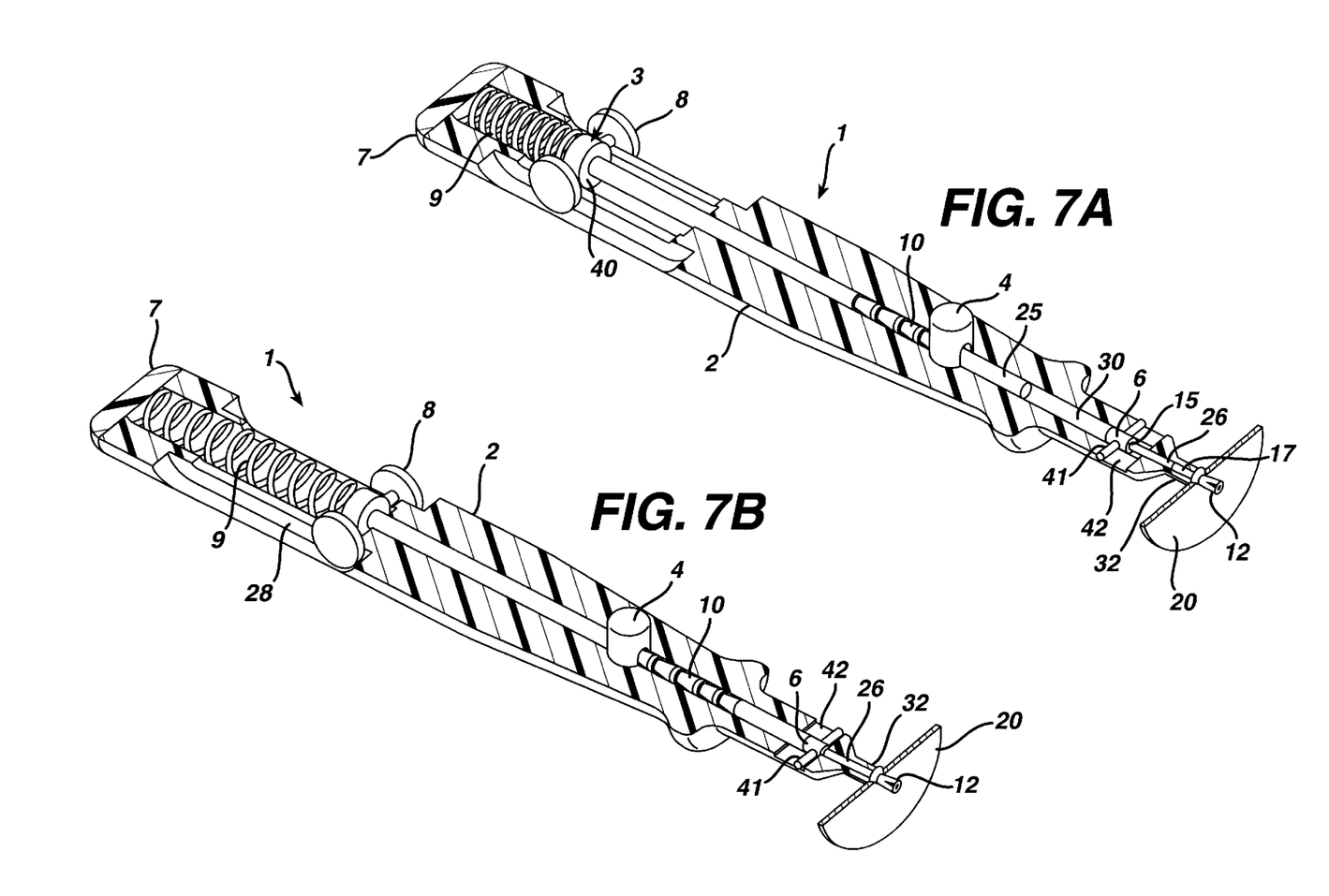
FIG. 7A illustrates the position of the applier mechanism and rivet before firing.
FIG. 7B illustrates the rivet applier after deploying a rivet into a plate.
Figures 8A, 8B:
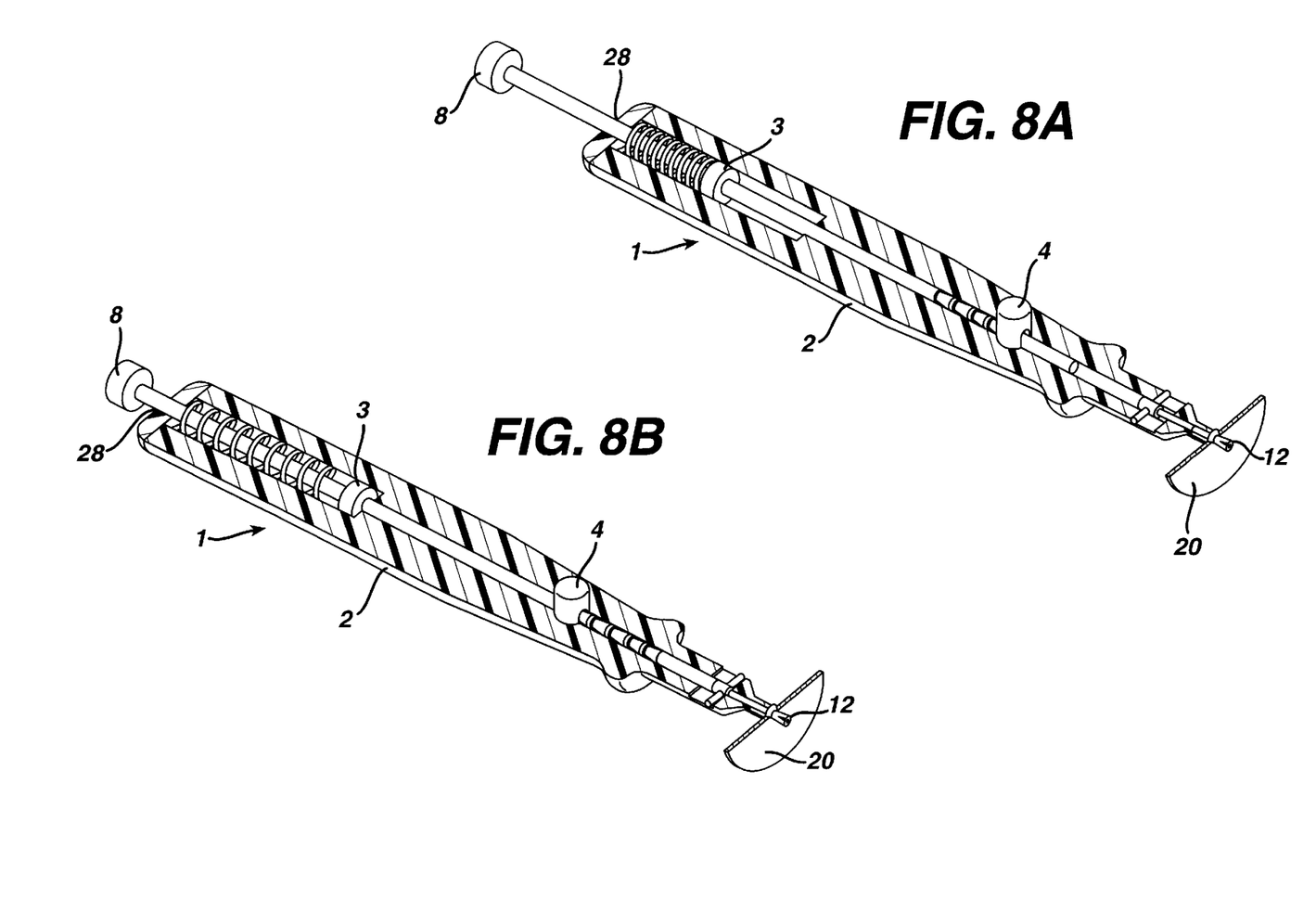
FIG. 8A illustrates the position of the applier mechanism and rivet before firing.
FIG. 8B illustrates the rivet applier after deploying the rivet.

The applier 1 is fired when the trigger mechanism 4, is depressed, releasing the trigger notch 11 from the hammer notches 10. The hammer 3 accelerates toward the firing pin 6 and impacts the firing pin 6 and in turn impacts the rivet pin 17. The hammer 3 ceases moving distally when the hammer stop 40 encounters the hammer chamber wall 39. Similarly the firing pin and firing pin guide will cease moving distally when the firing pin stop 15 and the firing pin guide stop 41 encounter the passage wall 16 and the guide opening wall 42 (FIGS. 3 and 7). This is advantageous for precisely controlling the rivet pin travel. The device will not allow a rivet pin to over-travel due to three stops incorporated into the device. Additional firing shots can be taken without loading a new rivet by re-cocking the hammer 3 using the loading grips 8 and pushing the trigger 4. The firing action of the rivet applier 1 allows the rivet applier to deploy a rivet 12 into a plate 20 (or other medical device) with minimal force and minimal recoil (see FIG. 6).

Varying levels of impact force can be achieved by pulling the hammer 3 further in the proximal direction or by removing the cap 7 and changing the hammer spring 9.

Figure 9:
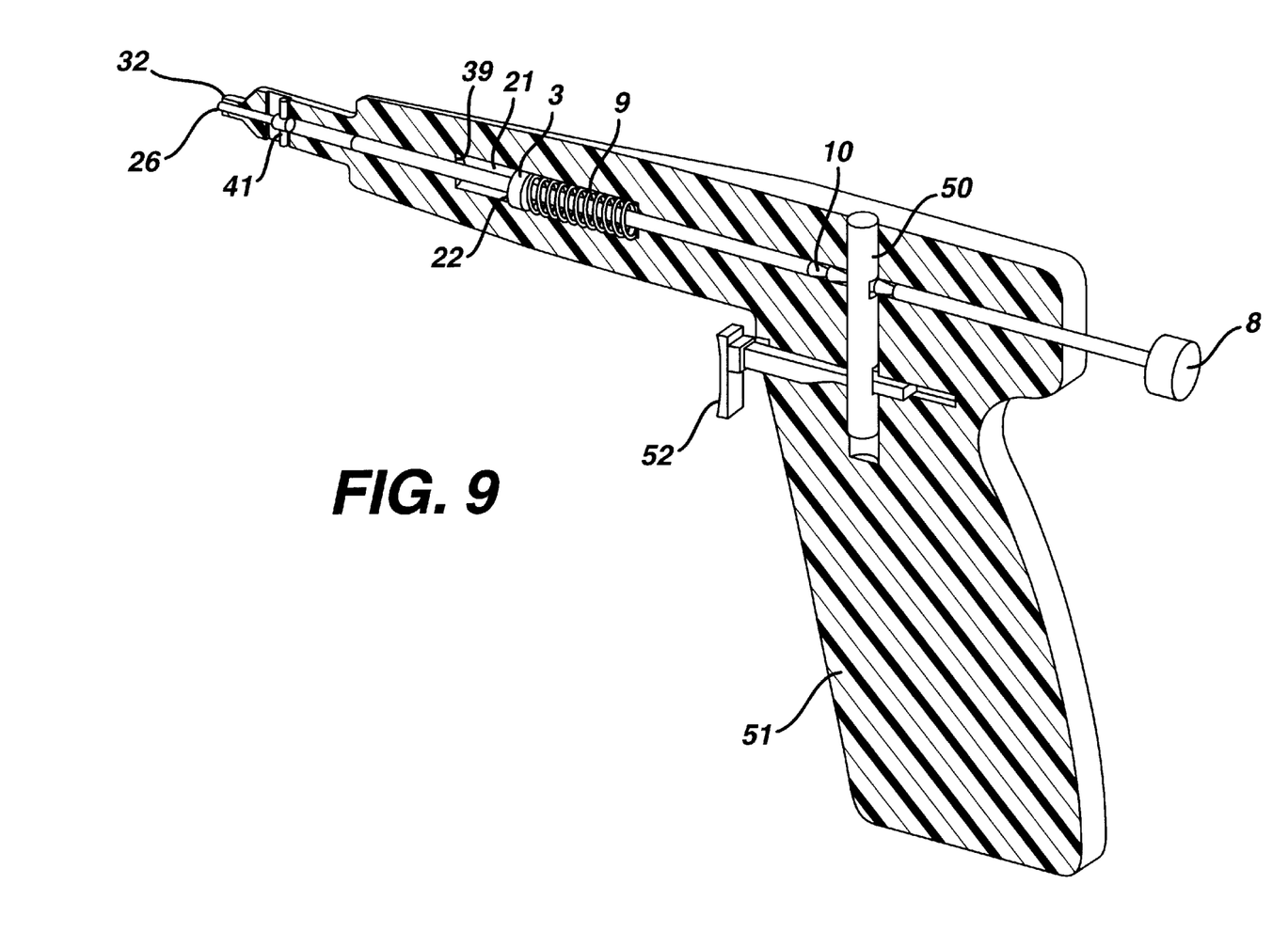
FIG. 9 is a perspective view of a third embodiment of a rivet applier.

FIG. 9 displays a third embodiment to the single shot rivet applier in which a gun handle 51 may be incorporated. The trigger pin 50 is linked to cam trigger 52. When the cam trigger 52 is depressed the trigger pin 50 releases the hammer 3. The resulting movement of the hammer 3 is the same as the previously described firing action.

We claim:

1. A rivet applier comprising a body having a central axis, a proximal end and a distal end, adjacent to the proximal end of the body aligned along the central axis is a hammer chamber that contains a hammer slidably mounted in said hammer chamber, the hammer is biased by a hammer spring toward the distal end of the rivet applier and mechanically linked to a loading grip by an opening extending through the body for moving the hammer from a first position to a second position, at the distal end of the applier is a receiver for retaining rivets, the receiver is in mechanical communications with a firing pin slidably mounted within the body by a passage that is aligned substantially along the central axis of the body and connected to the hammer chamber, wherein the hammer when moved from the first position to the second position contacts the firing pin which in turn is driven into the receiver, wherein the firing pin comprises a head and extending therefrom a striker pin, and wherein the firing pin has extending therefrom, substantially perpendicular to a central axis of the firing pin, at least one firing guide.

2. The rivet applier of claim 1 wherein the hammer is composed of a head and a striker rod extending from the head.

3. The rivet applier of claim 2 wherein the rivet applier has a trigger mechanism.

4. The rivet applier of claim 3 wherein the trigger mechanism comprises a trigger pin with a trigger notch.

5. The rivet applier of claim 4 wherein the trigger mechanism has a spring to bias the trigger notch into the striker rod.

6. The rivet applier of claim 5 wherein the striker rod has hammer notches to engage the trigger notch on the trigger pin.

7. The rivet applier of claim 2 wherein the hammer has a hammer stop.

8. The rivet applier of claim 7 wherein the receiver has an end and the hammer stop is positioned to stop the hammer striker from driving the firing pin striker beyond the end of the receiver.

9. The rivet applier of claim 1 wherein the firing pin has a firing pin stop.

10. The rivet applier of claim 9 wherein the firing pin stop is position to stop the firing pin striker from extending beyond the receiver.

11. The rivet applier of claim 1 wherein the at least one firing guide is positioned to stop the firing pin striker from extending beyond the receiver.

12. The rivet applier of claim 1 wherein the body has extending therefrom a gun handle.

13. The rivet applier of claim 12 wherein a trigger mechanism is placed in the gun handle.

* * * * *